United States Patent
Horcajada et al.

(10) Patent No.: US 11,166,965 B2
(45) Date of Patent: *Nov. 9, 2021

(54) COMPOSITIONS FOR USE IN STIMULATING BONE GROWTH

(71) Applicant: Société des Produits Nestlé S.A., Vevey (CH)

(72) Inventors: Marie Noelle Horcajada, Echenevex (FR); Fanny Membrez, Cugy (CH); Elizabeth Offord Cavin, Montreux (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/870,224

(22) Filed: May 8, 2020

(65) Prior Publication Data

US 2020/0316094 A1    Oct. 8, 2020

Related U.S. Application Data

(63) Continuation of application No. 14/780,265, filed as application No. PCT/EP2014/056569 on Apr. 2, 2014, now Pat. No. 10,675,290.

(30) Foreign Application Priority Data

Apr. 5, 2013  (EP) .................................... 13162445

(51) Int. Cl.
| | | |
|---|---|---|
| *A61K 31/593* | (2006.01) | |
| *A61K 31/05* | (2006.01) | |
| *A61K 31/592* | (2006.01) | |
| *A61K 31/351* | (2006.01) | |
| *A23L 33/155* | (2016.01) | |
| *A23L 33/16* | (2016.01) | |
| *A61K 31/7048* | (2006.01) | |
| *A61K 45/06* | (2006.01) | |
| *A61K 47/02* | (2006.01) | |

(52) U.S. Cl.
CPC .......... *A61K 31/593* (2013.01); *A23L 33/155* (2016.08); *A23L 33/16* (2016.08); *A61K 31/05* (2013.01); *A61K 31/351* (2013.01); *A61K 31/592* (2013.01); *A61K 31/7048* (2013.01); *A61K 45/06* (2013.01); *A61K 47/02* (2013.01); *A23V 2002/00* (2013.01)

(58) Field of Classification Search
CPC ......... A23L 1/303; A23L 1/304; A61K 31/05; A61K 31/351; A61K 31/592; A61K 31/593; A61K 31/7048; A61K 45/06; A61K 47/02
USPC ........................................................ 514/27
See application file for complete search history.

(56) References Cited

U.S. PATENT DOCUMENTS

| | | | |
|---|---|---|---|
| 7,662,408 B2 | 2/2010 | Saito et al. | |
| 8,841,264 B2 | 9/2014 | Raederstorff et al. | |
| 2004/0162292 A1 | 8/2004 | Evanstad et al. | |
| 2006/0009425 A1 | 1/2006 | Delgado-Herrera et al. | |
| 2006/0162292 A1 | 7/2006 | Liempd Van | |
| 2006/0193931 A1* | 8/2006 | Coxam | A61P 19/08 424/769 |
| 2007/0020350 A1 | 1/2007 | Numano et al. | |
| 2007/0154532 A1 | 7/2007 | Tutino et al. | |
| 2013/0005682 A1 | 1/2013 | Raedestrorff et al. | |
| 2016/0136108 A1 | 5/2016 | Raederstorff | |

FOREIGN PATENT DOCUMENTS

| | | |
|---|---|---|
| DE | 10257478 | 7/2004 |
| JP | 2007-517792 | 7/2007 |
| JP | 2010-500964 | 1/2010 |
| JP | 2010-524867 | 7/2010 |
| NL | 2005194 | 2/2012 |
| WO | 2007112996 | 11/2007 |
| WO | 2008006581 | 1/2008 |
| WO | 2009121600 | 10/2009 |
| WO | 2009132807 | 11/2009 |

OTHER PUBLICATIONS

Shokuhin Kogyo (Food industry), Apr. 15, 1997, vol. 40, No. 7, pp. 64-69 (a document teaching well known art).
Shokuhin to Kagaku (Food and Science), 2007, vol. 49, No. 7, pp. 79-81 (a document teaching well-known art).
Mediterranean Journal of Nutrition and Metabolism, Oct. 2008, vol. 1, Issue 2, pp. 117-120.
Japanese Office Action Appl. No. P2016-505801 dated Jan. 9, 2018 (English Translation) 4 pages.
Japanese Office Action Appl. No. P2016-505801 dated Jan. 9, 2018 5 pages.
Chuin et al., "Effect of antioxidants combined to resistance training on BMD in elderly women: a pilot study", Osteoporosis International, vol. 20, No. 7, Jul. 2009, pp. 1253-1258.
"Often called 'sunshine vitamin,' vitamin D helps bone strength", Neswok, Retrieved on May 28, 2018, Webpage avaiiable at: https://newsok.comtarticie/3165 766/often-ca iied-su nshi ne-vitarnin-vita min-d-hel ps-bone-strength, 2 pages.
"Olive Extracts Reduce Osteoporosis Bone Loss", Discount Vitamins & Herbs, Retrieved on May 28, 2018, Webpage avaiiable at: http://www.discount-vitamins-herbs net/n-343-bone-olive.htrn, 2 pages.
Eryuan Liao, "P?1armacologica! Mechanism and Clinical Application of Vitamin D Formulations", Centrai SouH1 Pharmacy, (2003) vol. 1., No. 2, pp. 98-102, published on Jun. 30, 2003.
Chinese Office Action for Application No. 201480018027.1 dated Dec. 12, 2017—1 0 pages.
Chinese Office Action for Application No. 201480018027.1 dated Dec. 12, 2017—7 pages (English Translation).
Hagiwara et al. "Olive polyphenol hydroxytryrosol prevents bone loss" European Journal of Pharmacology, 2011, vol. 662, pp. 78-84.

* cited by examiner

*Primary Examiner* — Shaojia A Jiang
*Assistant Examiner* — Michael C Henry
(74) *Attorney, Agent, or Firm* — K&L Gates LLP

(57) ABSTRACT

The present invention relates to use of a composition for maintenance of bone and/or cartilage health or prevention, alleviation and/or treatment of bone and/or cartilage disorders.

18 Claims, 6 Drawing Sheets

COMPOSITIONS FOR USE IN STIMULATING BONE GROWTH

PRIORITY CLAIMS

This application is a continuation of U.S. patent application Ser. No. 14/780,265 filed Sep. 25, 2015, which is a U.S. national stage application under 35 USC § 371 of International Appl. No. PCT/EP14/56569 filed Apr. 2, 2014, which claims priority to European Application No. 13162445.4 filed Apr. 5, 2013. The entire contents of the above-referenced applications are hereby expressly incorporated herein by reference.

FIELD OF THE INVENTION

The present invention relates to use of a composition for maintenance of bone and/or cartilage health or prevention, alleviation and/or treatment of bone and/or cartilage 5 disorders.

BACKGROUND

Bone mass evolves throughout life and is regulated by genetic, mechanical and hormonal mechanisms. Bone mineral acquisition occurs during childhood and peak bone mass is achieved around 20 years of age. During this period, bone formation exceeds bone resorption. Later in life, and particularly around the time of the menopause, or in the elderly population, bone mass and quality are impaired due to a higher bone turnover with excessive bone resorption leading to a gradual loss of bone mass, microarchitecture, structure and strength.

To maintain bone, it is important to restore the balance between bone formation and bone resorption. This bone remodelling process is regulated at the bone cell level involving a tight interaction between bone forming cells (osteoblasts) and bone resorbing cells (osteoclasts).

In a healthy adult, manor animal, the joint action of the osteoblasts and osteoclasts makes possible the maintenance of the bone mass over time and simultaneously ensures remodelling of bone tissue by resorption and de novo synthesis of bone.

In a healthy adult, the rate of formation of the osteoclasts and osteoblasts is such that a balance is struck between bone formation and bone resorption. However, in osteoporotic individuals, an imbalance in the process of bone remodelling is produced which culminates in a loss of bone which proceeds at a more rapid rate than the rate of formation. Although this imbalance exists to a certain extent in most individuals as they age, it is much more severe and occurs at a younger age in osteoporotic individuals.

Thus, in man and other mammals a great variety of disorders are related to abnormal metabolism of bone resorption and bone formation, leading to an imbalance in metabolism or bone remodelling.

Moreover, in man and animals, there are many conditions characterised by the need to increase bone formation. For example, in the case of bone fractures, it is necessary to stimulate bone growth in order to accelerate complete repair of the bone. This need is also present in the periodontal diseases, the metastatic diseases of bone, the osteolytic diseases and the conditions under which repair of the connective tissue is required, for example for the cicatrisation or regeneration of defects or traumatisms of cartilage. The stimulation of bone growth is also required in the case of primary and secondary hyperparathyroidism, as well as in osteoporosis associated with diabetes and in osteoporosis associated with glucocorticoids.

Although there exists today a large variety of active compounds for stimulating bone formation and/or inhibiting bone resorption, there is a constant need for new active compounds, in particular owing to the limited success of the current treatments.

Another joint disorder is osteoarthritis, which is a first cause of disability in the elderly. Currently, no cure exists for osteoarthritis and therapy is only palliative aiming at improving symptoms.

SUMMARY

In a surprising manner, the applicant has shown that a combination of Vitamin D with hydroxytyrosol and/or oleuropein, which are polyphenois derived from the olive tree, is capable of acting synergistically to stimulate bone formation and/or cartilage anabolism. The combination is able, via stimulation of osteoblast differentiation and activity and collagen synthesis, to stimulate bone formation, as well as cartilage anabolism. The addition of the combination of Vitamin D with either or both oleuropein or hydroxytyrosol results in a stimulation of osteoblasts which is both increased in strength, and moved forward in time (i.e. the stimulation is elicited earlier than with either component on its own). In the context of this application, the effect of addition of Vitamin D is referred to as "potentiating" the effect of polyphenois on bone formation and/or cartilage anabolism.

Thus, the invention in a first aspect relates to a composition comprising Vitamin D for use to potentiate the effects of one or more polyphenols on bone formation and/or cartilage anabolism.

In a further aspect the invention relates to a composition comprising vitamin D and one or more polyphenols for use to potentiate the stimulation of bone formation and/or cartilage 35 anabolism by said polyphenols.

In a further aspect the invention relates to composition for use according to the invention comprising vitamin D and one or more polyphenols is administered at least once per day, for a time period of at least 2 months, preferably at least 3 months.

In a further aspect, the invention relates to a pharmaceutical composition comprising Vitamin D and one or more polyphenols.

In yet a further aspect, the invention relates to a method of treatment, alleviation and/or prophylaxis of a bone and/or cartilage disorder, comprising administering an effective amount of Vitamin D in combination with one or more polyphenols to an individual in need thereof.

BRIEF DESCRIPTION OF THE FIGURES

In all figures, 1,25(OH)2D3=$10^{-9}$ M 1,25 dihydroxyvitamin D3; OLP=1 µM Oleuropein; HTy=1 µM Hydroxytyrosol; C+=optimized medium use as positive control; C−=minimal medium use as negative control Data were expressed as mean SEM (3 replicates). Statistics: Kruskal Wallis test followed by Mann Whitney U test (2 tailed) *$p<0.05$; $p<0.01$; *$p<0.001$ vs negative control (C−)

DETAILED DESCRIPTION

Definitions

Prior to discussing the present invention in further details, the following terms and conventions will first be defined:

In the context of the present invention, mentioned percentages are weight/weight percentages unless otherwise stated.

The term "and/or" used in the context of the "X and/or Y" should be interpreted as "X", or "Y", or "X and Y".

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 4 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the ad.

Composition Comprising Vitamin D for Use

Polyphenols have previously been shown to have beneficial effects on inflammation and bone metabolism.

Figure 2:
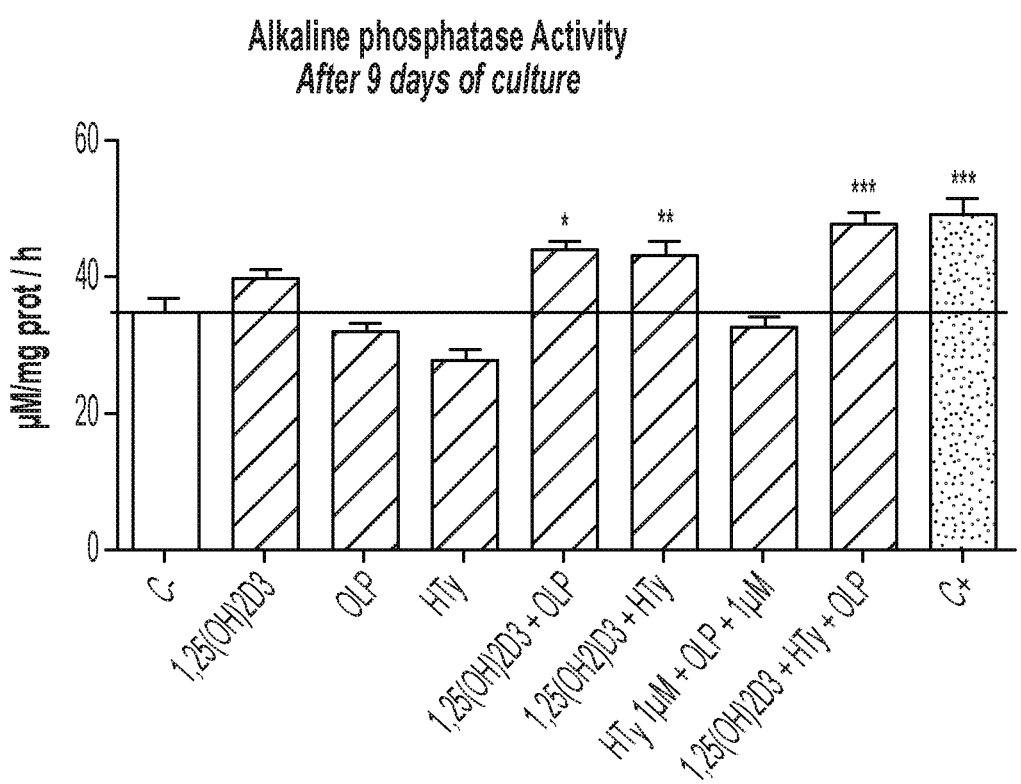
FIG. 2 shows alkaline phosphatase (ALP) activity after 9 days of culture, indicated by micromolar ALP per milligram of protein per hour in response to with a combination of 1,25(OH)2D3, OLP and HTy.

The inventors have surprisingly shown that the combination of Vitamin D with one or more polyphenols, such as one or more of HT and OLP, potentiates the stimulating effects of these polyphenols on bone formation and/or cartilage anabolism (see Example 2 and discussion thereof, and FIG. 2).

By "stimulation of bone formation and/or cartilage anabolism" is meant the capacity of the combination of Vitamin D, oleuropein and hydroxytyrosol to stimulate the activity of osteoblasts and thus promote the synthesis of the protein networks of bone and/or cartilage. This leads to the deposition of minerals, in particular calcium, in these protein networks, i.e. to stimulate the mineralisation of the bone, also called bone formation, and to the stimulation of cartilage anabolism.

By "potentiate the stimulating effects of the polyphenols" is meant that the stimulating effect of the one or more polyphenols is both increased in strength and brought forward in time (i.e. elicited earlier than in the absence of Vitamin D) by the addition of Vitamin D.

Thus, the invention in a first aspect relates to a composition comprising Vitamin D for use to potentiate the effects of one or more polyphenols on bone formation and/or cartilage anabolism. The polyphenols may be for example one or more of oleuropein and hydroxytyrosol.

Vitamin D may be present in any suitable form. Various useful forms of vitamin D are available including, for example, cholecalciferol (D3), ergocalciferol (D2), and their biologically active metabolites and precursors such as, 1-alpha-hydroxy Vitamin D, 25¬30 hydroxy vitamin D, 1, 25-dihydroxy vitamin D and the like.

In one embodiment of this aspect of the invention, Vitamin D may be provided simultaneously with, or sequentially to the provision of the one or more polyphenols. The Vitamin D may be provided in the same composition as the one or more polyphenols, or may be provided in separate compositions, for example in a kit of parts, or a series of interacting products. If the Vitamin D and the one or more polyphenols are presented in one or more separate compositions, they may be mixed prior to administration, or may be administered simultaneously or sequentially.

The potentiating effect of Vitamin D is evident already in combination with a single polyphenol, such as in combination with oleuropein or hydroxytyrosol.

The potentiating effect is even further increased when Vitamin D is given in combination 5 with both oleuropein and hydroxytyrosol.

In a further aspect, the invention relates to use of Vitamin D in the manufacture of a composition or medicament, to potentiate the effects of one or more polyphenols an bone formation and/or cartilage anabolism.

Composition for Use

In a further aspect, the invention relates to a composition comprising vitamin D and one or more polyphenols for use to potentiate the stimulation of bone formation and/or cartilage anabolism by said polyphenols.

The polyphenols may be for example olive polyphenols, such as for example polyphenols selected from the group consisting of oleuropein, ligstroside, hydroxytyrosol and or tyrosyl. In a preferred embodiment, the olive polyphenols comprise one or more of oleuropein and hydroxytyrosol, even more preferred the polyphenols comprise oleuropein and hydroxytyrosol.

Compositions according to the invention may for example comprise Vitamin D in an amount of from 800 to 1,200 IU per serving. The one or more polyphenols may each be present in amount of from 0.01 mg to about 1 g, preferably from 0.1 mg to 1 g, even more preferably from 1 mg to about 1 g per serving.

The effective amount of a composition according to the present invention which is required to achieve a therapeutical effect will, of course, vary with the particular composition, the route of administration, the age and condition of the recipient, and the particular disorder or disease being treated.

As an illustration, a RTD (ready to drink) supplemented with combination of Vitamin D, hydroxytyrosol and oleuropein will contain from 0.01 mg to 500 mg of each active ingredient per serving.

In one embodiment a composition of the invention comprises for example from 800 to 1,200 IU Vitamin D, such as 800 to 1100, 800 to 1,000, 850 to 1,000, 850 to 950, 900 to 950, such as for example about 900, or about 950 IU. In further embodiments a composition of the invention comprises in addition to Vitamin D, also an amount of from 0.01 mg to 1 g of oleuropein, such as an amount of from 0.01 mg to 500 mg, for example from 0.1 mg to 500 mg, 0.5 mg to 500 mg, 1 mg to 500 mg, 10 mg to 500 mg, 20 mg to 500 mg, 50 mg to 500 mg, 100 mg to 500 mg, 250 mg to 500 mg, 300 mg to 500 mg, 350 mg to 500 mg, 400 mg to 500 mg; or such as from 400 mg to 1 g, such as for example from 500 mg to 1 g, 550 mg to 1 g, 600 mg to 1 g, 650 mg to 1 g, 750 mg to 1 g, 800 mg to 1 g, 900 mg to 1 g; or such as from 550 mg to 950 mg, for example from 600 mg to 900 mg, 700 mg to 800 mg. The embodiment may further comprise Hydroxytyrosol in an amount for for example 0.01 mg to 1 g, such as such as an amount of from 0.01 mg to 500 mg, for example from 0.1 mg to 500 mg, 0.5 mg to 500 mg, 1 mg to 500 mg, 10 mg to 500 mg, 20 mg to 500 mg, 50 mg to 500 mg, 100 mg to 500 mg, 250 mg to 500 mg, 300 mg to 500 mg, 350 mg to 500 mg, 400 mg to 500 mg; or such as from 400 mg to 1 g, such as for example from 500 mg to 1 g, 550 mg to 1 g, 600 mg to 1 g, 650 mg to 1 g, 750 mg to 1 g, 800 mg to 1 g, 900 mg to 1 g; or such as from 550 mg to 950 mg, for example from 600 mg to 900 mg, 700 mg to 800 mg.

In a preferred embodiment, a composition of the invention comprises from 800 to 1,200 IU Vitamin D, from 0.01 mg to 1 g Oleuropein, and from 0.01 mg to 1 g hydroxytyrosol.

Nutritional Compositions

The compositions for use according to the invention may be nutritional compositions or pharmaceutical compositions, and may be for human or veterinary use.

In one embodiment, the composition for use according to the invention is a nutritional composition.

By "nutritional composition" is meant according to the invention, a composition containing the combination of Vitamin D, and one or more polyphenols, such as one or more olive polyphenols, such as one or more of oleuropein, ligstroside, hydroxytyrosol and or tyrosyl, preferably oleuropein and/or hydroxytyrosol, and constituting a dietary composition not possessing the characteristics of a medicine.

The nutritional compositions are understood to include any number of optional additional ingredients, including conventional food additives (synthetic or natural), for example one or more acidulants, additional thickeners, buffers or agents for pH adjustment, chelating agents, colorants, emulsifiers, excipient, flavor agent, mineral, osmotic agents, a pharmaceutically acceptable carrier, preservatives, stabilizers, sugar, sweeteners, texturizers, and/or vitamins. The optional ingredients can be added in any suitable amount. The nutritional products or compositions of the invention may be a source of complete nutrition or may be a source of incomplete nutrition.

As used herein, "complete nutrition" includes nutritional products and compositions that contain sufficient types and levels of macronutrients (protein, fats and carbohydrates) and micronutrients to be sufficient to be a sole source of nutrition for the animal to which it is being administered to. Patients can receive 100% of their nutritional requirements from such complete nutritional compositions.

As used herein, "incomplete nutrition" includes nutritional products or compositions that do not contain sufficient levels of macronutrients (protein, fats and carbohydrates) or micronutrients to be sufficient to be a sole source of nutrition for the animal to which it is being administered to. Partial or incomplete nutritional compositions can be used as a nutritional supplement.

The nutritional compositions of the invention may be a medical food. A medical food is a special class of nutritional composition designed to provide dietary management of certain conditions. The medical food meets certain criteria as set out by and regulated under the Orphan Drug Act of 1983 in Section 5 [360ee](b)(2)(D).

Ingredients

The compositions according to the invention may comprise one or more further bioactive molecules such as antioxidants, anti-inflammatory compounds, fatty acids, prebiotic fibres, probiotics, glucosamine, chondroitin sulphate, minerals, trace elements and/or vitamins.

Examples of minerals and trace elements which may be comprised in a nutritional composition according to the invention include mineral elements and trace elements such as calcium, magnesium, sodium, potassium, phosphorus, copper, zinc, iron selenium, chromium and molybdenum.

In preferred embodiments, the composition of the invention comprises the mineral calcium. The calcium may be one or more of for example an organic and/or inorganic physiologically acceptable compound, for example one or more of calcium inorganic salts (calcium chloride, calcium phosphate, calcium sulphate, calcium oxide, calcium hydroxide and/or calcium carbonate), calcium organic salts (such as calcium citrate, calcium maleate or mixtures thereof), and/or organic components which comprise calcium, such as powdered skimmed milk or calcium caseinate.

In preferred embodiments, the composition of the invention comprises the mineral magnesium. The magnesium may be one or more of for example an organic and/or inorganic physiologically acceptable compound, for example one or more of magnesium inorganic salts (such as magnesium chloride, magnesium phosphate, magnesium sulphate, magnesium oxide, magnesium hydroxide and/or magnesium carbonate), magnesium organic salts (such as magnesium citrate, magnesium maleate or mixtures thereof), and/or organic components which comprise magnesium.

Thus, a preferred embodiment of the composition of the inventions comprises the mineral calcium and/or magnesium.

One or more antioxidants may also be present in the nutritional compositions. Non-limiting examples of antioxidants include astaxanthin, carotenoids, coenzyme Q10 ("CoQ10"), flavonoids, glutathione, Goji (wolfberry), hesperidin, lactowolfberry, lignan, lutein, lycopene, polyphenols, selenium, vitamin A, vitamin C, vitamin E, zeaxanthin, or combinations thereof.

In an embodiment, the nutritional compositions include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

The nutritional compositions may include one or more probiotics. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, non-replicating microorganisms, or combinations thereof.

The nutritional compositions may include fiber or a blend of different types of fiber. The fiber blend may contain a mixture of soluble and insoluble fibers. Soluble fibers may include, for example, fructooligosaccharides, acacia gum, inulin, agar-agar, an alginate, carob bean, carrageenan, gum arabic, guar gum, karaya gum, pectin or xanthan gum, etc., these soluble fibres being in a hydrolysed or non-hydrolysed form. Insoluble fibers may include, for example, pea outer fiber.

A nutritional composition according to the invention may also comprise one or more further vitamins selected from vitamin A, vitamin E, vitamin K, vitamin C, folic acid, thiamine, riboflavin, vitamin B6, vitamin B12, niacin, biotin and pantothenic acid.

In an embodiment, the nutritional compositions include a source of protein. The protein source may be dietary protein including, but not limited to animal protein (such as milk protein, meat protein or egg protein), vegetable protein (such as soy protein, wheat protein, rice protein, and pea protein), or combinations thereof. In an embodiment, the protein is selected from the group consisting of whey, chicken, corn, caseinate, wheat, flax, soy, carob, pea or combinations thereof.

In an embodiment, the nutritional compositions include a source of carbohydrates. Any suitable carbohydrate may be used in the present nutritional compositions including, but not limited to, starch, sucrose, lactose, glucose, fructose, corn syrup solids, maltodextrin, modified starch, amylose starch, tapioca starch, corn starch, xylitol, sorbitol or combinations thereof.

In an embodiment, the nutritional compositions include a source of fat. The source of fat may include any suitable fat or fat mixture. For example, the fat source may include, but is not limited to, vegetable fat (such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like), animal fats (such as milk fat), or combinations thereof. The source of fat may also be less refined versions of the fats listed above (e.g., olive oil for polyphenol content).

In addition, a nutritional composition according to the invention may also comprise natural or artificial flavours, for example fruit flavours like banana, orange, peach, pineapple or raspberry or other plant flavours like vanilla, cocoa, coffee, etc.

A nutritional composition according to the invention may comprise a quantity of Vitamin D, and one or more of oleuropein and Hydroxytyrosol suitable for a daily oral administration included from 0.01 mg to 500 mg of each component.

The quantity of calcium contained in a nutritional composition according to the invention is adapted for a daily administration, provided by the said composition, included between 100 mg and 1,000 mg, preferably between 200 mg and 700 mg and very preferably between 300 mg and 600 mg of calcium.

Nutritional Composition Formats

Suitable nutritional composition formats according to the present disclosure include, for example, infant formulas, solutions, ready-for-consumption compositions (e.g. ready-to-drink compositions or instant drinks), liquid comestibles, soft drinks, juice, sports drinks, milk drinks, milk-shakes, yogurt drinks, soup, etc. In a further embodiment, the nutritional compositions may be manufactured and sold in the form of a concentrate, a powder, or granules (e.g. effervescent granules), which are diluted with water or other liquid, such as milk or fruit juice, to yield a ready-for-consumption composition (e.g. ready-to-drink compositions or instant drinks).

Further nutritional composition formats include, dairy products, baked products, dairy products, desserts, confectionery products, cereal bars, breakfast cereals. Examples of dairy products include milk and milk drinks, yoghurts and other cultured milk products, ice creams and cheeses. Examples of baked products include bread, biscuits and cakes. Examples of formulas include nutritionally complete formula.

In one embodiment, the composition for use according to the invention may also be available in a great variety of formats designed as animal foods, in particular for the dog or the cat, whether in a wet form, semi-wet form or dry form, in particular in the form of biscuits.

Routes of Administration

The nutritional compositions of the present disclosure may be administered by any means suitable for human administration, and in particular for administration in any part of the gastrointestinal tract. Enteral administration, oral administration, and administration through a tube or catheter are all covered by the present disclosure. The nutritional compositions may also be administered by means selected from oral, rectal, sublingual, sublabial, buccal, topical, etc.

If the nutritional compositions are formulated to be administered orally, the compositions may be a liquid oral nutritional supplement (e.g., incomplete feeding) or a complete feeding. In this manner, the nutritional compositions may be administered in any known form including, for example, tablets, capsules, liquids, chewables, soft gels, sachets, powders, syrups, liquid suspensions, emulsions and solutions in convenient dosage forms.

In soft capsules, the active ingredients are preferably dissolved or suspended in suitable liquids, such as fatty oils, paraffin oil or liquid polyethylene glycols. Optionally, stabilizers may be added.

The nutritional compositions of the present disclosure may be a source of either incomplete or complete nutrition. The nutritional compositions may be administered by oral administration or tube feeding. If the nutritional compositions are formulated to be administered orally, the compositions may be a liquid oral nutritional supplement or feeding. The nutritional compositions may also be used for short term or long term tube feeding.

Composition for Use—Disorders and Target Groups

The inventors have shown that the compositions according to the invention results in increased stimulation of osteoblasts, indicative of increased bone formation and/or cartilage anabolism.

In one embodiment, the use according of to the invention is use is in the prevention, alleviation and/or prophylaxis of disorders linked to an imbalance in the relationship between bone formation and bone resorption, and/or linked to cartilage turnover, by potentiating the stimulation of bone formation and/or cartilage anabolism.

The composition for use according to the invention may be for use for the maintenance of the bone and/or cartilage status of the individual to whom it is administered, for example by administration of a composition according to the invention.

Compositions according to the invention may be useful for example for stimulating bone formation and cartilage anabolism in young individuals in the growth phase, in order to increase the bone density attained at the beginning of adult age and to increase the maximal bone mass (peak bone mass) at the beginning of adult age.

The compositions may further be useful for stimulating bone formation and/or cartilage anabolism in adults in order to increase maximal bone mass. Thus, the compositions may be useful for stimulating bone formation and/or cartilage anabolism for example in women such as perimenopausal women, in healthy adults and/or in healthy ageing adults such as healthy adults and/or healthy ageing adults who are pre-osteoarthritic, or in adults who have been diagnosed with a disorder of the bone and/or cartilage such as osteoarthritis, osteoporosis, and/or a fracture event.

The compositions according to the invention may in other embodiments be useful for example in preventing the bone loss that occurs with ageing.

The compositions according to the invention may in other embodiments be useful for 5 maintaining or improving joint functionality, including bone and cartilage functionality during ageing.

Compositions according to the invention may in some embodiments be useful to improve bone strength.

In a further embodiment, a composition for use according to the invention relates to use in treatment of disorders in bone formation and/or cartilage anabolism such as osteoporosis, Paget's disease, bone loss or osteolysis observed near a prosthesis, metastatic bone diseases, hyperthyroidism, hypocalcemia due to a cancer, multiple myelomas, periodontal diseases, osteoarthritis, bone deficit resulting from a fracture or fracture healing.

In preferred embodiments the invention relates to the composition for use according to the invention, wherein the disorder is osteoporosis and/or osteoarthritis.

In a further embodiment, the composition for use according to the invention relates to use for treating a bone deficit resulting from a fracture.

The composition for use according to the invention may result in an improved bone formation and/or regeneration, and/or cartilage anabolism, during fracture healing. It may be useful to reduce risk of osteoporosis and improve recovery alter fracture.

Compositions of the invention may help to prevent bone loss, in particular bone loss associated with age in mammals or bone loss associated with long term hospitalization.

Furthermore, it may help to build cartilage in mammals and prevent osteoarthritis in pets and humans, which results in a better activity or mobility of the individual (e.g. pets and/or humans).

Thus, in particular, the composition according the invention may be for use to improve activity and/or mobility of the individual, for example by treating, alleviating or preventing osteoarthritis, and/or by improving bone strength.

A particular embodiment of the invention relates to the composition for use to improve activity and/or mobility of the individual, for example by treating, alleviating or preventing osteoarthritis, and/or by improving bone strength, in elderly or aging individuals.

In further embodiments, the composition for use according to the invention may be for use in mammals, such as humans, or pets. Examples of pets include cats, dogs, and horses.

Though the invention may be useful in many various age groups, in a preferred embodiment the compositions for use according to the invention are targeted to ageing population, in particular elderly patients.

Method of Manufacturing a Nutritional Composition of the Invention

The invention relates in a further aspect to a method for manufacturing a nutritional composition of the invention, said method comprising the steps of:

providing a nutritional composition; and adding to the nutritional composition one or more of Vitamin D, and one or more polyphenols, such that the prepared nutritional composition comprises a combination of Vitamin D and one or more polyphenols.

In embodiments of this aspect of the invention, the polyphenols may for example be olive polyphenols, for example one or more selected from oleuropein, ligstroside, hydroxytyrosol and or tyrosyl, preferably one or more of oleuropein and hydroxytyrosol, even more preferably, both oleuropein and hydroxytyrosol.

Pharmaceutical Composition

In a further aspect, the invention relates to a pharmaceutical comprising Vitamin D and one or more polyphenols, such as olive polyphenols, such as selected from oleuropein, ligstroside, hydroxytyrosol and or tyrosyl, preferably oleuropein and/or hydroxytyrosol. The pharmaceutical may be a human composition. It may alternatively be a veterinary composition, for example suited for a dog, cat, or horse, in particular a thoroughbred horse.

By pharmaceutical means a composition, other than a nutritional composition, wherein a substance is used an or in the body to prevent, diagnose, alleviate, treat, or cure a disease in humans or animals in medicine.

In one preferred embodiment, the pharmaceutical composition of the invention comprises Vitamin D and oleuropein and/or hydroxytyrosol.

The invention further relates to uses of the pharmaceutical according to the invention, as described above as use of the compositions of the invention.

A pharmaceutical composition according to the invention comprises Vitamin D and one or more polyphenols in combination with at least one excipient selected from the group constituted by the pharmaceutically acceptable excipients. Procedures for the preparation of pharmaceutical compositions according to the invention can easily be found by the specialist skilled in the art, for example in the handbook Remington's Pharmaceutical Sciences, Mid. Publishing Co, Easton, Pa., USA. Physiologically acceptable excipients, vehicles and adjuvants are also described in the handbook entitled "Handbook of Pharmaceutical Excipients, Second edition, American Pharmaceutical Association, 1994. In order to formulate a pharmaceutical composition according to the invention, the specialist skilled in the art will advantageously be able to refer to the latest edition of the European Pharmacopoeia or the Pharmacopoeia of the United States of America (USP). The specialist skilled in the art will in particular be able advantageously to refer to the fourth edition "2002" of the European Pharmacopoeia or also to the edition USP 25-NF 20 of the American Pharmacopoeia (U.S. Pharmacopoeia).

Advantageously, a pharmaceutical composition such as defined above is suitable for oral, parenteral or intravenous administration. When the pharmaceutical composition according to the invention comprises at least one pharmaceutically or physiologically acceptable excipient, it is in particular an excipient appropriate for administration of the composition by the oral route or an excipient suitable for administration of the composition by the parenteral route.

A pharmaceutical composition comprising vitamin D and one or more polyphenols according to the invention is available indifferently in a solid or liquid form. For oral administration, a solid pharmaceutical composition in the form of tablets, capsules or gelatine capsules will be preferred.

In liquid form, a pharmaceutical composition in the form of an aqueous or non-aqueous suspension, or also in the form of a water-in-oil or oil-in-water emulsion will be preferred. Solid pharmaceutical forms may comprise, as vehicles, adjuvants or excipients, at least one diluent, one flavour, one solubilising agent, one lubricant, one suspension agent, one binder, one disintegrating agent and one encapsulating agent. Such compounds are for example magnesium carbonate, magnesium stearate, talc, lactose, pectin, dextrin, starch, gelatine, cellulosic materials, cocoa butter, etc. The compositions in liquid form may also comprise water, possibly as a mixture with propylene glycol or polyethylene glycol, and possibly also colouring agents, flavours, stabilisers and thickening agents.

Method of Treatment

The invention also relates to a method treatment, alleviation and/or prophylaxis of a disorder linked to an imbalance in bone and/or cartilage metabolism, in particular a disorder associated with loss of bone mass and/or loss or cartilage, the said method comprising administering to a patient an effective amount of a composition of the invention to an individual in need thereof. For example, the method comprises administering an effective amount of Vitamin D in combination with one or more polyphenols.

As used herein, "effective amount" is an amount that prevents a deficiency, treats a disease or medical condition in an individual or, more generally, reduces symptoms, manages progression of the diseases or provides a nutritional, physiological, or medical benefit to the individual.

The effective amount of a composition according to the present invention which is required to achieve a therapeutical effect will, of course, vary with the particular composition, the route of administration, the age and condition of the recipient, and the particular disorder or disease being treated.

The invention further provides methods of increasing bone formation and/or cartilage anabolism, increasing bone mineral density during growth and optimizing peak bone mass, of treating or preventing osteoarthritis, and/or of stimulating bone formation and/or cartilage anabolism during fracture healing which comprises administering an effective amount of a composition of the invention to an individual.

In one embodiment, the invention relates to a method for the treatment, alleviation and/or prophylaxis of a disorder linked to an imbalance in bone metabolism, in particular a disorder associated with loss of bone mass, said method comprising a step of administering a therapeutically efficacious quantity of Vitamin D and one or more polyphenols, or a pharmaceutical composition containing Vitamin D and one or more polyphenols, to an individual in need thereof.

In one embodiment, the method of treatment according to the invention concerns treatment, alleviation and/or prophylaxis of osteoarthritis.

The methods of treatment according to the invention may be in a mammal, such as a human, or a pet, for example a dog, a cat and/or a horse.

In certain embodiments the composition of the invention to be administered in the method of treatment, may be one or more nutritional compositions of the invention and/or pharmaceutical compositions of the invention.

Dosage Regime

The invention relates to the surprising finding that the combination of Vitamin D with one or more polyphenols, such as hydroxytyrosol and/or oleuropein, potentiates the bone formation and/or cartilage anabolism effect of said polyphenols.

The combination can both increase the effect of the polyphenols, and elicit and earlier response from the osteoblasts. Thus, compositions of the invention may be useful in treatment with shorter durations, in contrast to the long term treatment times used for conventional treatments of e.g. osteoarthritis.

Therefore, the invention also relates to a use according to the invention, wherein a composition of the invention is administered at least once a day for a time period of at least 1 month, such as at least 2 months, preferably at least 3 months.

In other embodiments the invention relates to a use according to the invention, wherein a composition is administered at least once a day for at least 1 month.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1—Collagen Synthesis by Osteoblasts

Primary osteoblasts were isolated from the calvaria of newborn Wistar rats by enzymatic digestion as described by Declercq et al. in 2004. During all experiments, cells were maintained in α-minimal essential medium with 10% heat-inactivated fetal bovine serum and 1% penicillin/streptomycin under conditions of 5% CO2 and 37° C. Cells were seeded an Coll-1-coated 96-well plates at a density of 3500 cells/well or in 24-well plates at a density of 3×104 cells/well and cultured for 2 days in a-MEM to reach confluence. Cells were then exposed to different conditions: minimal medium (C−), minimal medium containing 50 µg/ml ascorbic acid, 5 mM ß-glycerophosphate (C+; optimized medium), and minimal medium supplemented with 1 µM Oleuropein (OLP) or/and 1 µM Hydroxytyrosol (HTy) or/and $10^{-9}$ M 1,25 dihydroxyvitamin D3 (1,25(OH)2D3). OLP and HTy were dissolved in dimethylsulfoxide (DMSO) and 1,25(OH)2D3 was dissolved in ethanol. The final concentrations of DMSO and ethanol in the medium were 0.1% each. The medium was changed every 2 days.

After 9 days, cellular collagen content was measured using the Sircol Assay from Biocolor. This Sircol Collagen Assay is a quantitative dye-binding method designed for the analysis of collagens extracted from mammalian tissues and cells during in vitro culture. The dye reagent binds specifically to the [Gly-X-Y]n helical structure found in mammalian collagens (Types I-V).

Figure 1:
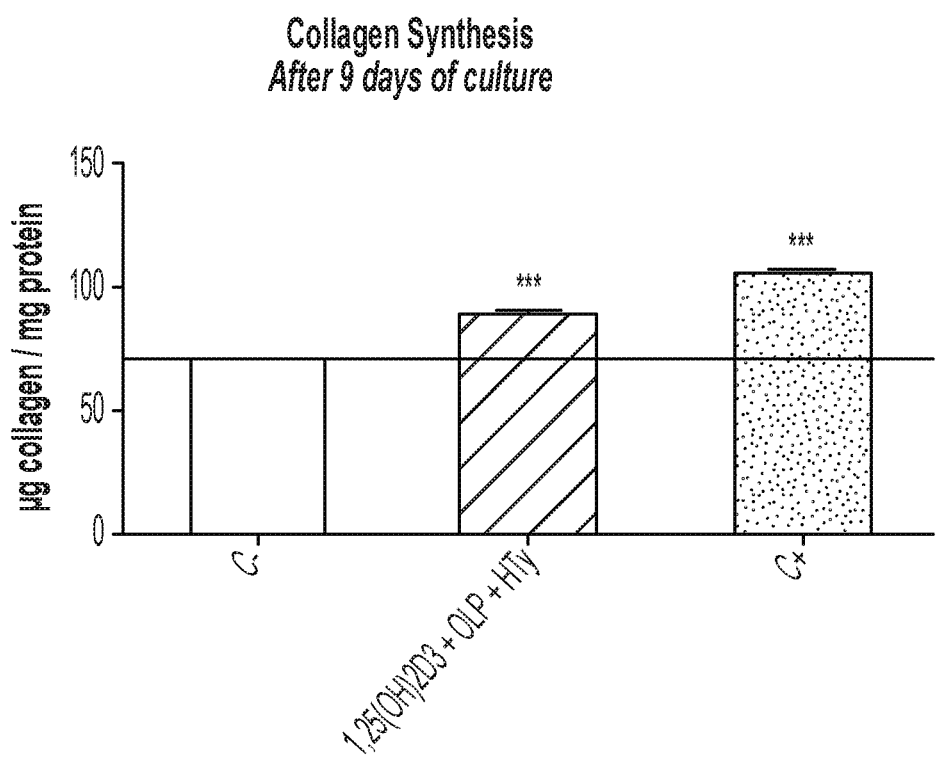
FIG. 1 shows collagen synthesis by osteoblasts after 9 days of culture, measured by micrograms of collagen produced per milligram of total protein in response to stimulation with a combination of 1,25(OH)2D3 OLP and HTy.

FIG. 1 shows collagen synthesis by osteoblasts after 9 days of culture, measured by micrograms of collagen produced per milligram of total protein in response to stimulation with a combination of 1,25(OH)2D3 OLP and HTy.

1,25(OH)2D3=$10^{-9}$ M 1,25 dihydroxyvitamin D3; OLP=1 μM Oleuropein; HTy=1 μM Hydroxytyrosol; C+=optimized medium use as positive control.

Data were expressed as mean SEM (3 replicates). Statistics: Kruskal Wallis test followed by Mann Whitney U test (2 tailed) *$p<0.05$; $p<0.01$; *$p<0.001$ vs negative control (C−)

As is shown in FIG. 1, the addition of a combination of 1,25(OH)2D3, OLP and HTy stimulates significantly the cellular collagen synthesis of the osteoblasts after 9 days of culture.

Example 2—Alkaline Phosphatase Activity of Osteoblasts

Primary osteoblasts were isolated from the calvaria of newborn Wistar rats by enzymatic digestion as described by Declercq et al. in 2004. During all experiments, cells were maintained in α-minimal essential medium with 10% heat-inactivated fetal bovine serum and 1% penicillin/streptomycin under conditions of 5% CO2 and 37° C. Cells were seeded on Coll-1-coated 96-well plates at a density of 3500 cells/well or in 24-well plates at a density of $3 \times 10^4$ cells/well and cultured for 2 days in o-MEM to reach confluence. Cells were then exposed to different conditions: minimal medium (C−), minimal medium containing 50 μg/ml ascorbic acid, 5 mM ß-glycerophosphate (C+; optimized medium), and minimal medium supplemented with 1 μM Oleuropein (OLP) or/and 1 pM Hydroxytyrosol (HTy) or/and $10^{-9}$ M 1,25 dihydroxyvitamin D3 (1,25(OH)2D3). OLP and HTy were dissolved in dimethylsulfoxide (DMSO) and 1,25(OH)2D3 was dissolved in ethanol. The final concentrations of DMSO and ethanol in the medium were 0.1% each. The medium was changed every 2 days.

Enzymatic activity of Alkaline Phosphatase (ALP) was measured kinetically on Treatment Days 0, 5, 9, 12 and 15. Osteoblasts were rinsed twice with PBS before being frozen on dry ice. The cells were then lysed by freeze-thaw cycle and homogenization into 200 pl of 1 M diethanolamine and 0.24 mM magnesium chloride buffer pH 9.8 (ALP buffer). Cell lysates (10 μl) were added to 200 pl of 6 mg/mI solution of p-nitrophenyl phosphate (p NPP) in ALP buffer. Absorbance was measured at 405 nm and 30° C., and every 2 min 30 s for 30 min using a VarioSklan Flash microplate reader. ALP activity was expressed as micromoles of p-NPP per hour per milligram of protein. Protein measurement was performed in accordance with the method of Bradford using Quick Start BioRad protein assay.

FIG. 2 shows alkaline phosphatase (ALP) activity after 9 days of culture, indicated by micronnolar ALP per milligram of protein per hour in response to with a combination of 1,25(OH)2D3, OLP and HTy.

C−=minimal medium use as negative control; 1,25(OH)2D3=$10^{-9}$ M 1,25 dihydroxyvitamin D3; OLP=1 μM Oleuropein; HTy=1 μM Hydroxytyrosol; C+=optimized medium use as positive control.

Data were expressed as mean SEM. Statistics: Kruskal Wallis test followed by Mann Whitney U test (2 tailed) *$p<0.05$; $p<0.01$; *$p<0.001$ vs negative control (C−).

FIG. 2 further demonstrates that the addition of a combination of 1,25(OH)2D3, OLP and HTy stimulates significantly the cellular collagen synthesis of the osteoblasts alter 9 days of culture.

FIGS. 3 to 6 shows Alkaline phosphatase (ALP) activity of osteoblasts cultured in the presence of 1,25(OH)2D3, oleuropein (OLP), hydroxytyrosol (Hyt); separately or in combinations in a time course model.

C−=minimal medium use as negative control; 1,25(OH)2D3=$10^{-9}$ M 1,25 dihydroxyvitamin D3; OLP=1 pM Oleuropein; HTy=1 μM Hydroxytyrosol; C+=optimized medium use as positive control.

Data were expressed as mean SEM. Statistics: Kruskal Wallis test followed by Mann Whitney U test (2 tailed) *$p<0.05$; $p<0.01$; *$p<0.001$ vs negative control (C−).

CONCLUSIONS

Figure 3:
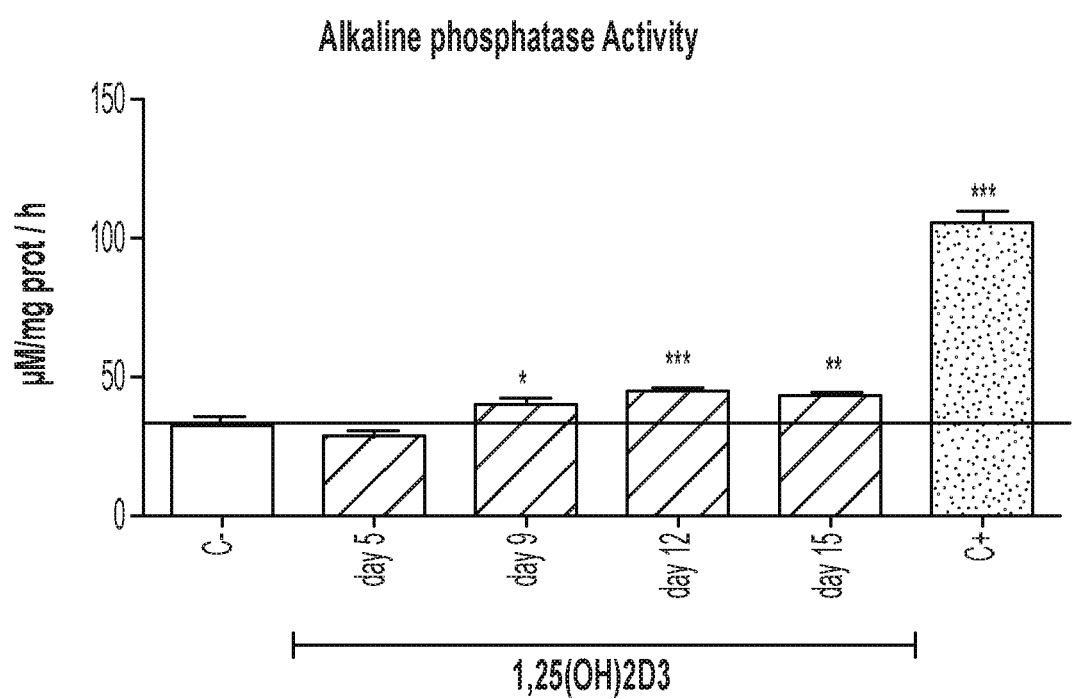
FIG. 3 shows Alkaline phosphatase (ALP) activity of osteoblasts cultured in the presence of 1,25(OH)2D3 after 5, 9, 12 or 15 days of treatment.
Figure 4A:
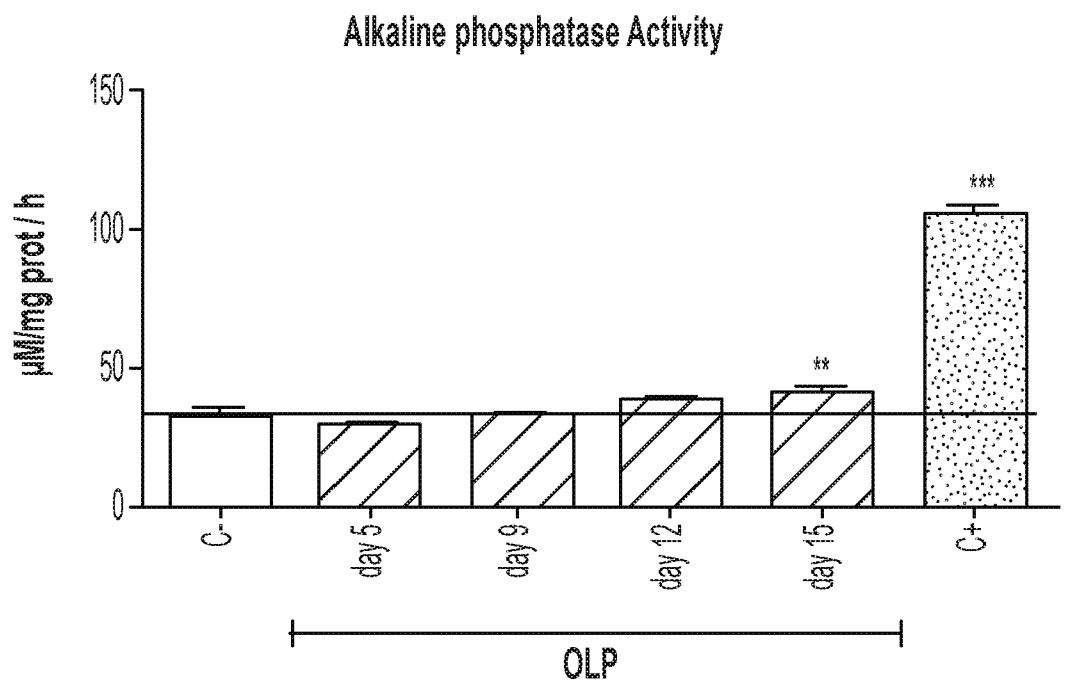
FIG. 4A shows Alkaline phosphatase (ALP) activity of osteoblasts cultured in the presence of Oleuropein after 5, 9, 12 or 15 days of treatment.
Figure 4B:
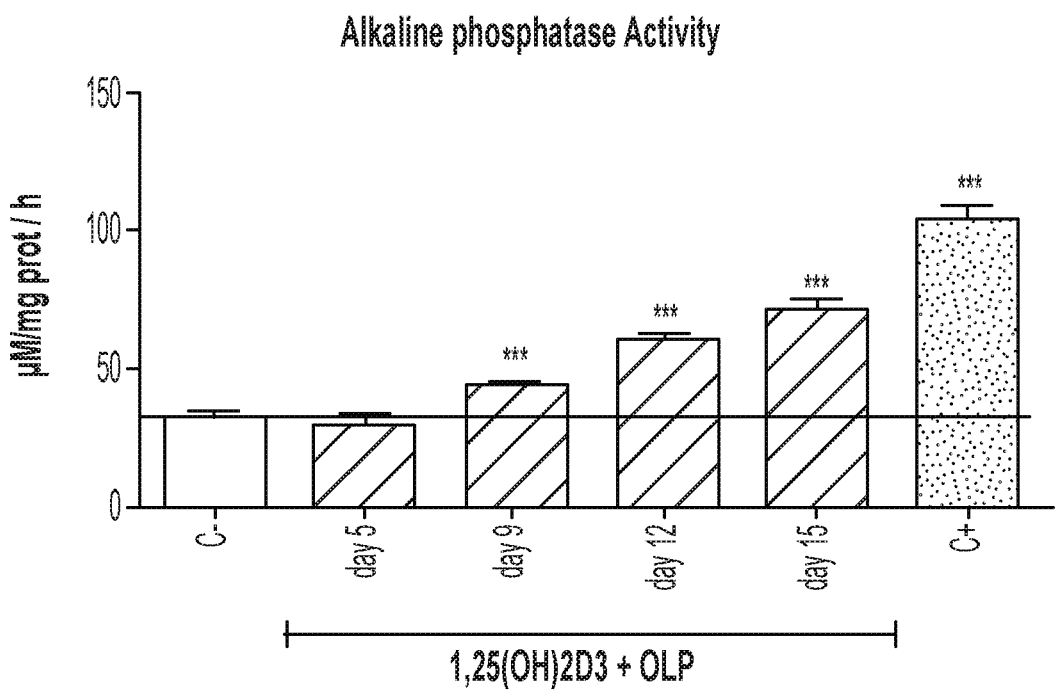
FIG. 4B shows Alkaline phosphatase (ALP) activity of osteoblasts cultured in the presence of 1,25(OH)2D3 and Oleuropein after 5, 9, 12 or 15 days of treatment.
Figure 5A:
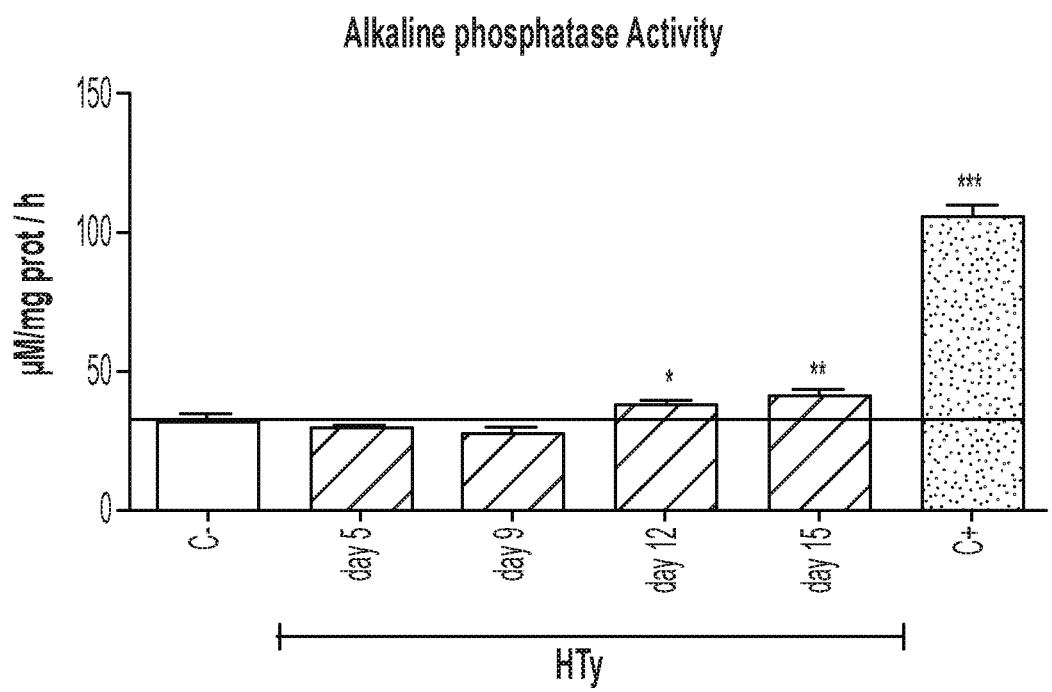
FIG. 5A shows Alkaline phosphatase (ALP) activity of osteoblasts cultured in the presence of Hydroxytyrosol after 5, 9, 12 or 15 days of treatment.
Figure 5B:
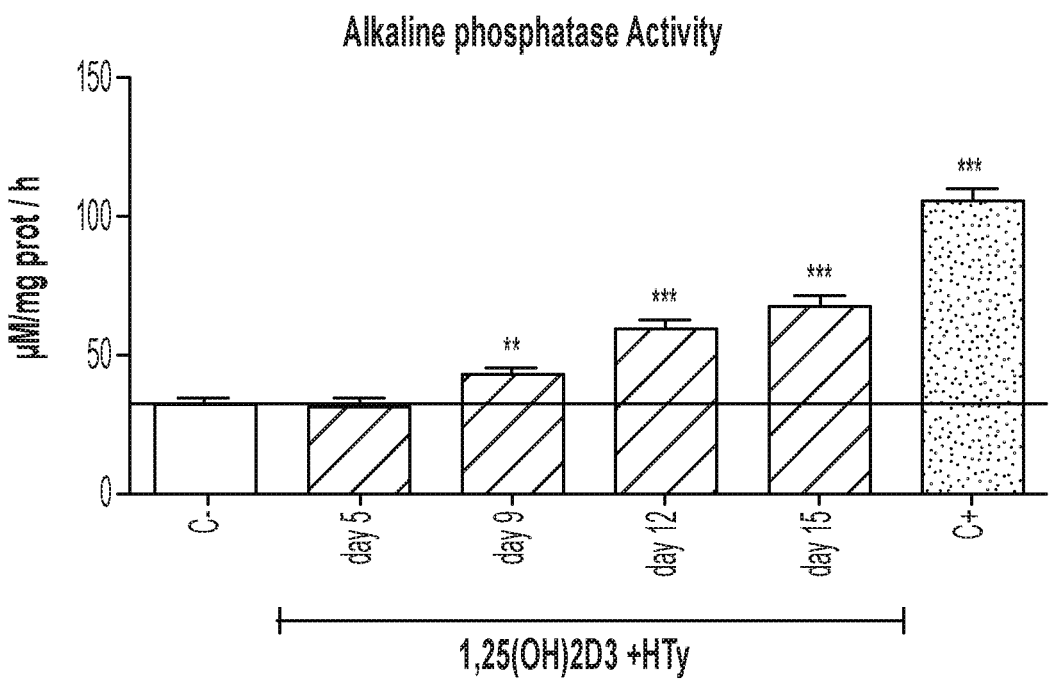
FIG. 5B shows Alkaline phosphatase (ALP) activity of osteoblasts cultured in the presence of 1,25(OH)2D3 and Hydroxytyrosol after 5, 9, 12 or 15 days of treatment.
Figure 6A:
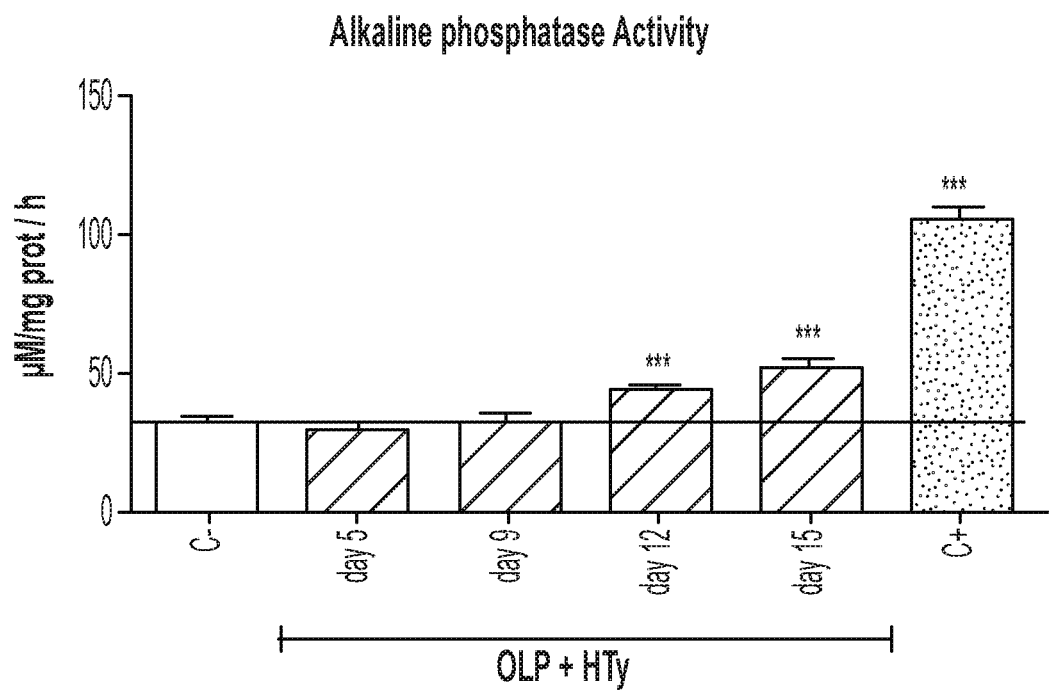
FIG. 6A shows Alkaline phosphatase (ALP) activity of osteoblasts cultured in the presence of Oleuropein and Hydroxytyrosol after 5, 9, 12 or 15 days of treatment.
Figure 6B:
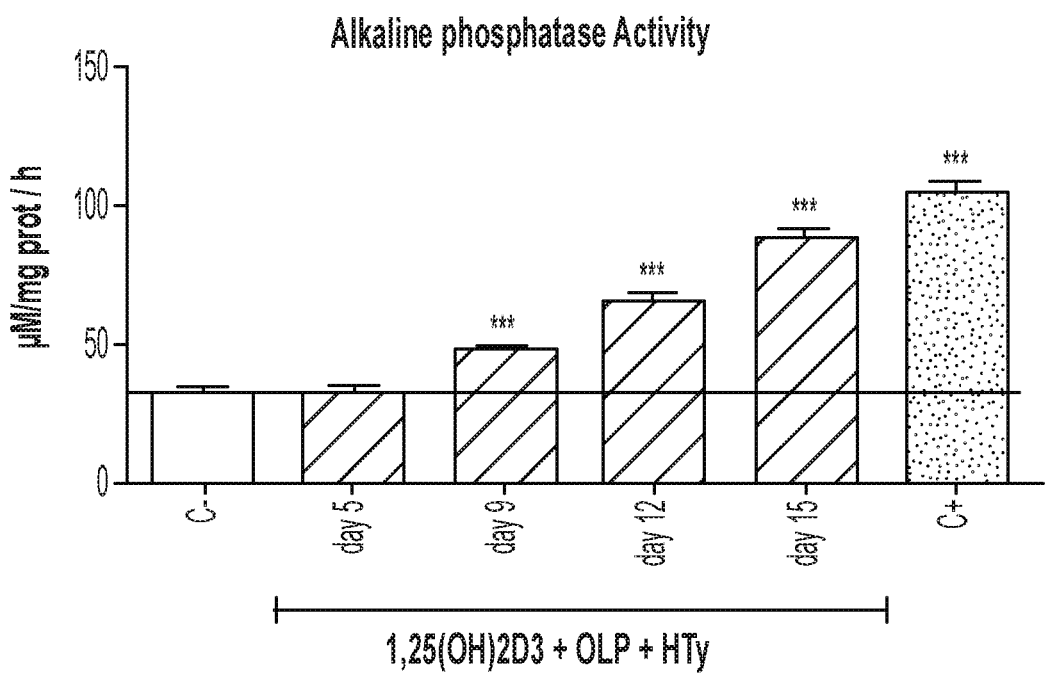
FIG. 6B shows Alkaline phosphatase (ALP) activity of osteoblasts cultured in the presence of 1,25(OH)2D3, Oleuropein and Hydroxytyrosol after 5, 9, 12 or 15 days of treatment.

As can be seen from the data shown in FIG. 3, the addition of Vitamin D3 in itself does induce a small but statistically significant increase in AP activity on day 15, indicative of osteoblast activity and bone formation and/or cartilage anabolism. In the same manner, the addition of either HT on its own or OLP on its own also results in a small increase on day 15, comparable with the effect of Vitamin D3 (see respective figures).

Combining both HT and OLP does also increase the osteoblast activity (again, looking at day 15), but not as much as combining Vitamin D with either HT or OLP. Still, the only points with statistically significant difference from control are day 12 and day 15. Earlier measurements, at day 5 and day 9, do not differ statistically from negative control.

Thus, the data presented illustrate two effects of addition of Vitamin D. Firstly, the addition of Vitamin D together with either one or both of the HT and OLP increases the osteoblast response. This is seen in comparison of for example levels at Day 15.

Secondly, the addition of Vitamin D together with either one or both of the HT and OLP elicits osteoblast activity earlier than in the co. The conclusion is that addition of Vitamin D leads to an earlier response, and a stronger response. It is concluded that addition of Vitamin D potentiates the bone formation and/or cartilage anabolism response elicited by OLP and/or HT.

The invention is claimed as follows:

1. A method of potentiating effects of oleuropein on bone formation and/or cartilage anabolism, the method comprising orally administering an effective amount of a composition consisting essentially of vitamin D and oleuropein to an individual in need thereof, wherein the effective amount of the composition comprises 800 to 1,200 IU of the Vitamin D, and the composition is administered to the individual at least once per day, for a time period of at least one month.

2. The method of claim 1, wherein the effective amount of the composition comprises 850 to 1,000 IU of the Vitamin D.

3. The method of claim 1, wherein the effective amount of the composition comprises 900 to 950 IU of the Vitamin D.

4. The method of claim 1, wherein the effective amount of the composition comprises 0.01 mg to 1 g of the oleuropein.

5. The method of claim 1, wherein the effective amount of the composition comprises 0.1 mg to 1 g of the oleuropein.

6. The method of claim 1, wherein the effective amount of the composition comprises 1.0 mg to 1 g of the oleuropein.

7. The method of claim 1, wherein the individual has a disorder linked to an imbalance in the relationship between bone formation and/or cartilage anabolism and bone resorption, and the effective amount of the composition potentiates stimulation of cartilage anabolism in the individual.

8. The method of claim 7, wherein the disorder is osteoporosis.

9. The method of claim 1, wherein the effective amount of the composition maintains and/or improves mobility in the individual.

10. A method of treatment and/or alleviation of a disorder linked to an imbalance in bone and/or cartilage metabolism, the method comprising orally administering an effective amount of a composition consisting essentially of Vitamin D and oleuropein to an individual having the disorder, wherein the effective amount of the composition comprises 800 to 1,200 IU of the Vitamin D, and the composition is administered to the individual at least once per day, for a time period of at least one month.

11. The method of claim 10, wherein the effective amount of the composition comprises 850 to 1,000 IU of the Vitamin D.

12. The method of claim 10, wherein the effective amount of the composition comprises 900 to 950 IU of the Vitamin D.

13. The method of claim 10, wherein the effective amount of the composition comprises 0.01 mg to 1 g of the oleuropein.

14. The method of claim 10, wherein the effective amount of the composition comprises 0.1 mg to 1 g of the oleuropein.

15. The method of claim 10, wherein the effective amount of the composition comprises 1.0 mg to 1 g of the oleuropein.

16. The method of claim 10, wherein the composition is a pharmaceutical composition consisting of the Vitamin D, the oleuropein and at least one excipient.

17. The method of claim 10, wherein the disorder is osteoporosis.

18. The method of claim 10, wherein the effective amount of the composition maintains and/or improves mobility in the individual.

* * * * *